June 27, 1972 W. H. JESSEL, JR., ET AL Plant Pat. 3,221

CHRYSANTHEMUM PLANT

Filed Oct. 30, 1970 2 Sheets-Sheet 1

INVENTORS
WALTER H. JESSEL, JR.,
WILLIAM E. DUFFETT
BY Oberlin, Maky, Donnelly & Renner
ATTORNEYS INVENTORS
WALTER H. JESSEL, JR.,
WILLIAM E. DUFFETT
BY
Oberlin, Maky, Donnelly & Renner
ATTORNEYS

United States Patent Office

Plant Pat. 3,221
Patented June 27, 1972

3,221
CHRYSANTHEMUM PLANT

Walter H. Jessel, Jr., Doylestown, and William E. Duffett, Akron, Ohio, assignors to Yoder Brothers, Inc., Barberton, Ohio

Filed Oct. 30, 1970, Ser. No. 85,830
Int. Cl. A01h *5/00*
U.S. Cl. Plt.—80 1 Claim

The present invention comprises a new and distinct cultivar of chrysanthemum plant which is a sport of the very well known, non-patented cultivar, Escapade.

The new cultivar is similar in many respects to Escapade, having the same characteristics as Escapade of:

(1) Foliage shape.
(2) Sturdy stem and habit.
(3) Resistance to sunscald.
(4) Resistance to fade.
(5) Durability in shipment.

The new cultivar is distinguished from Escapade by the following characteristics, when grown side by side under identical conditions:

(1) Three inches to four inches more vigor.
(2) Three to four days later response.
(3) Three-fourths of an inch larger flower.
(4) Darker flower color.
(5) Twenty percent more petalage, providing a more solid flower.
(6) Foliage approximately 1" to 1½" longer in length and slightly more yellow-green in color.
(7) A longer recommended period of value in the northern and western states.

The new cultivar was selected from a flowering block of the parent cultivar in Barberton, Ohio. The cultivar has been asexually reproduced by cuttings at Barberton, Ohio, and has been found to retain its distinctive characteristics through successive propagations.

The new cultivar when grown in the vicinity of Barberton, Ohio, has a response period of approximately 9 weeks, and the following detailed description is based on observations made of the new cultivar in a greenhouse in Barberton, Ohio. The response time, blooming period, color, and total vigor may vary significantly with varying environmental conditions such as temperature, daylength, and light intensity. Suggested flowering in the northern and western United States is year-round; and in Florida, December through April.

Figure 1:
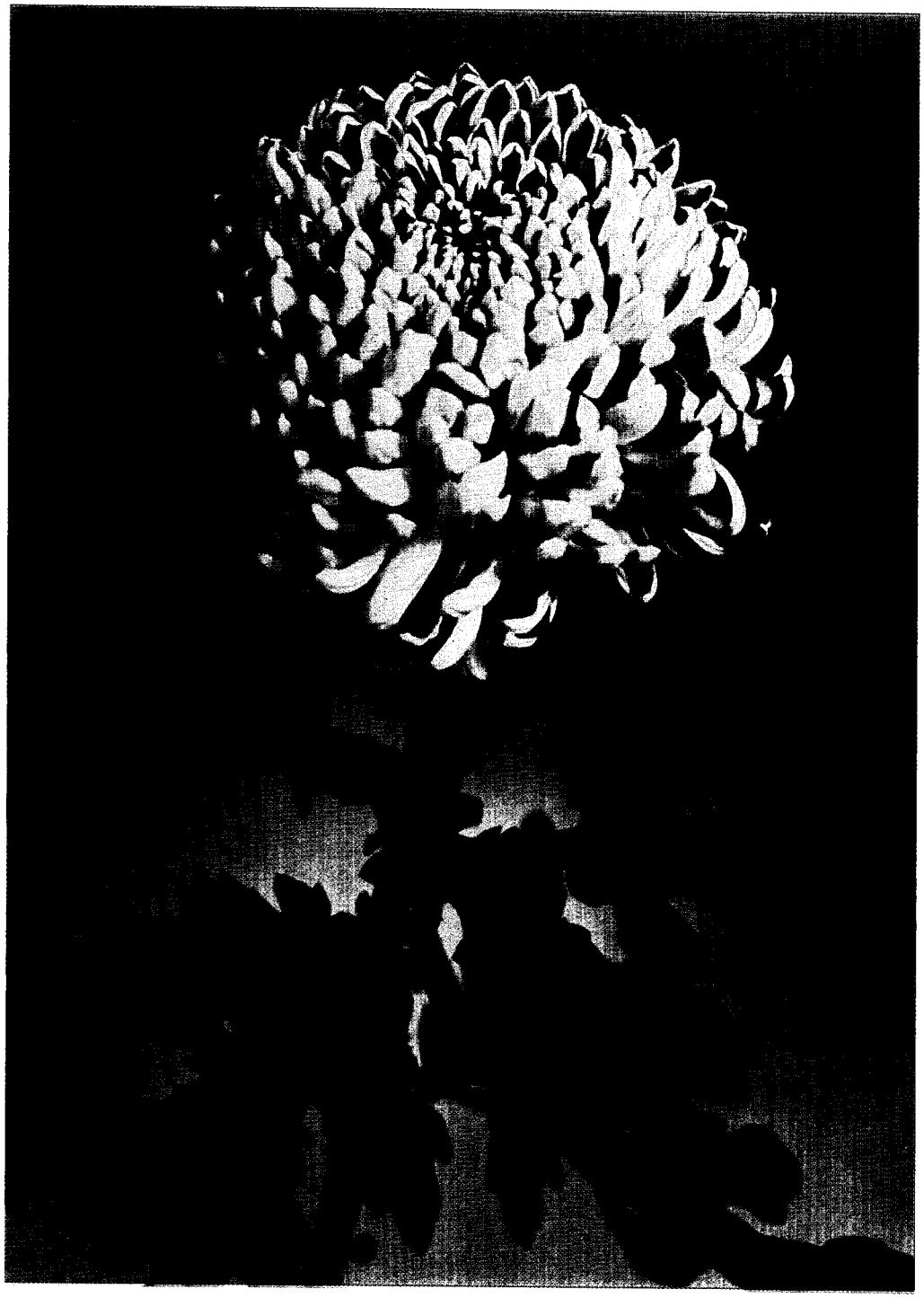
Figure 2:
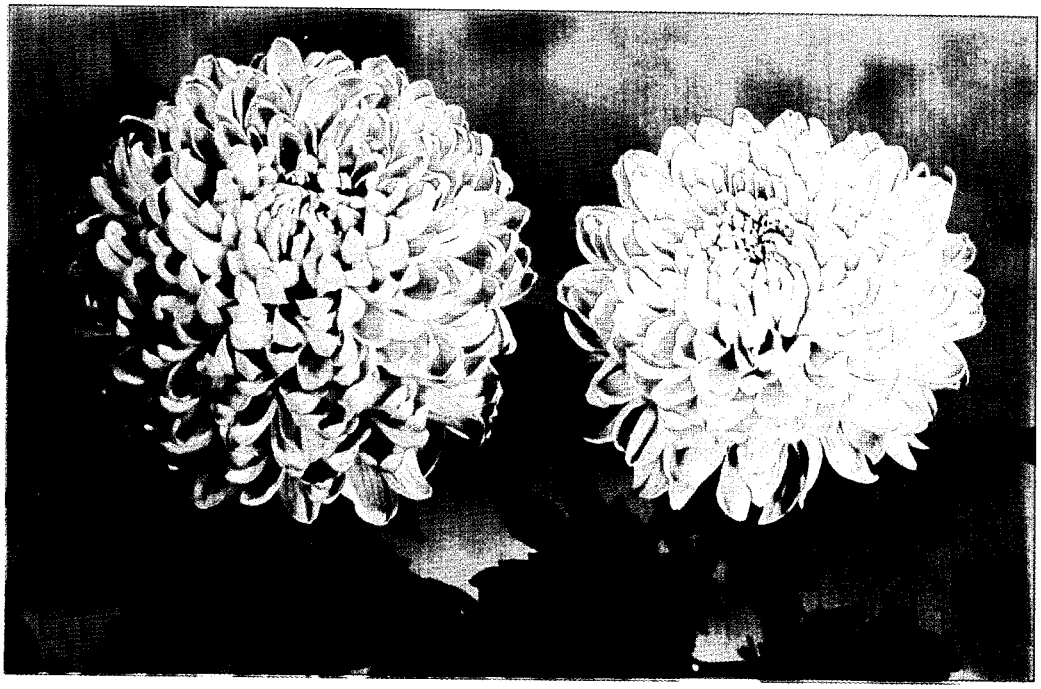

The accompanying darwings show the unique characteristics of the new cultivar, the colors being as nearly true as possible with color illustrations of this type. FIG. 1 comprises an enlarged view of the new cultivar, and FIG. 2 comprises a comparison view of the new cultivar and Escapade with the latter appearing on the right and the new cultivar on the left.

In the description which follows, color references are made to the Munsell Color Book, 1963 edition, and comparisons made with the parent cultivar Escapade.

BOTANICAL CLASSIFICATION

*Chrysanthemum morifolium*

| | Promenade | Escapade |
|---|---|---|
| Bloom: | | |
| Size | 5¾" | 5". |
| Fully expanded | 6½" | 5¾". |
| Borne | Singly on disbudded plant. | Singly on disbudded plant. |
| Stems | Heavy and strong | Heavy and strong. |
| Permanence | 7-10 days | 7-10 days. |
| Color: | | |
| Center of flower. | Dark lavender, 10P6/10. | Lavendar, 5RP6/6. |
| Base of petals | Yellow green, 2.5GY8/8 to lavender 10P7/8. | Grey-lavender, 5RP8/2. |
| Inside of petals | Lavender, 10P6/10 over light lavender, 10P9/1. | Lavender pink, 10P7/6. |
| Reverse of petals. | Lavender, 10P8/4 to light lavender, 10P9/1. | Pale lavender, 10P8/2. |
| Tonality from a distance. | Lavender | Lavender pink. |
| Discoloration | Light lavender, 10P6/10 over 10P9/1. | Pale lavender, 10P8/2. |

Petals:

*Texture.*—Smooth.
*Appearance and form.*—Very broad, slightly open at base, wide towards extremity. Tapers sharply.
*Arrangement.*—Composite, whorled on a single receptacle.
*Persistence.*—Resists shatter.
*Fragrance.*—Typical chrysanthemum.

Reproductive organs:

*Stamen, anthers.*—None.
*Pollen.*—None.
*Arrangement.*—Center of flower, if present.
*Styles.*—Present both ray and disc florets.
*Length.*—Short.
*Ovaries.*—Base of petal attached to receptacle.

Plant:

*Form.*—Herbaceous.
*Growth.*—Upright.
*Height.*—40"–42".
*Spread.*—None; little if grown pinched.

| | Promenade | Escapade |
|---|---|---|
| Foliage: | | |
| Top side | Dark green, 7.5GY2/4 | Dark green, 10GY2/4. |
| Size | 8¾" long, 5¼" wide | 7-8½" long, 5" wide. |
| Quantity | Numerous | Numerous. |
| Shape | Spatulate lobed | Spatulate lobed. |
| Texture | Smooth | Smooth. |
| Ribs and veins | Prominent | Prominent. |
| Edge | Deeply indented | Deeply indented. |
| Serration | Slight | Slight. |
| Underside | Light green, 7.5GY5/4 | Light green, 7.5GY5/4. |
| Stipules | Prominent | Prominent. |

We claim:

1. A new and distinct cultivar of chrysanthemum characterized particularly as to uniqueness when compared with the parent cultivar Escapade by its 3"–4" more vigor, 1"–1½" longer foliage, 3–4 days later response, ¾"–1" larger flower, darker flower color, 20 percent more petalage which provides a more solid flower, and slightly more yellow green foliage.

No references cited.

ROBERT E. BAGWILL, Primary Examiner